US010031057B2

(12) United States Patent
Romirer et al.

(10) Patent No.: US 10,031,057 B2
(45) Date of Patent: Jul. 24, 2018

(54) ROTATIONAL RHEOMETER FOR MEASURING POWDERY OR GRANULAR MATERIALS

(71) Applicant: ANTON PAAR GMBH, Graz-Strassgang (AT)

(72) Inventors: Richard Romirer, Graz (AT); Denis Schuetz, Graz (AT); Matthias Narnhofer, Graz (AT); Andreas Flecker, Voitsberg (AT)

(73) Assignee: Anton Paar GmbH, Graz-Strassgang (AT)

( * ) Notice: Subject to any disclaimer, the term of this patent is extended or adjusted under 35 U.S.C. 154(b) by 104 days.

(21) Appl. No.: 15/067,425

(22) Filed: Mar. 11, 2016

(65) Prior Publication Data
US 2016/0266022 A1 Sep. 15, 2016

(30) Foreign Application Priority Data
Mar. 11, 2015 (AT) .............................. A 50196/2015

(51) Int. Cl.
*G01N 11/14* (2006.01)
*G01N 11/00* (2006.01)

(52) U.S. Cl.
CPC ...... *G01N 11/14* (2013.01); *G01N 2011/0026* (2013.01)

(58) Field of Classification Search
CPC .................... G01N 2011/0026; G01N 11/14
USPC ........................................................ 73/54.28
See application file for complete search history.

(56) References Cited

U.S. PATENT DOCUMENTS

| 5,303,578 | A | * | 4/1994 | Williams | ............... G01N 11/10 73/54.23 |
| 5,321,974 | A | * | 6/1994 | Hemmings | ....... B01F 15/00201 73/54.31 |
| 6,065,330 | A | * | 5/2000 | Freeman | ................ G01N 11/14 73/54.28 |
| 6,167,752 | B1 | | 1/2001 | Raffer | |
| 2002/0014110 | A1 | * | 2/2002 | Bahia | ..................... G01N 11/14 73/54.01 |

(Continued)

FOREIGN PATENT DOCUMENTS

| AT | 404192 B | | 9/1998 | |
| GB | 2180343 A | * | 3/1987 | ............. G01N 11/14 |

(Continued)

*Primary Examiner* — Lisa Caputo
*Assistant Examiner* — Marrit Eyassu
(74) *Attorney, Agent, or Firm* — Lawrence A. Greenberg; Werner H. Stemer; Ralph E. Locher

(57) ABSTRACT

A rotational rheometer for measuring powdery or granular materials has a measuring container for receiving the product to be measured and a cover for the measuring container. A measuring body is held by a measuring shaft. The measuring body and the container are rotatable relative to one another. The measuring shaft is guided through the cover with low friction, or without contact altogether. An evaluation unit is arranged outside the measurement container to evaluate the measured values received by the measuring shaft. To seal the bearing gap or the passage of the measuring shaft in or through the cover in the measuring container, both a fluid seal with a sealing fluid inlet and at least a geometric seal cooperating with the fluid seal are provided as a powder barrier.

15 Claims, 4 Drawing Sheets

(56) References Cited

U.S. PATENT DOCUMENTS

| | | | | |
|---|---|---|---|---|
| 2002/0178842 A1* | 12/2002 | Taylor | ............... | E21B 21/067 |
| | | | | 73/863.12 |
| 2005/0132782 A1* | 6/2005 | Wallevik | ............. | B01F 7/063 |
| | | | | 73/54.28 |
| 2009/0137732 A1* | 5/2009 | Panz | ................. | C01B 33/193 |
| | | | | 524/588 |

FOREIGN PATENT DOCUMENTS

| | | |
|---|---|---|
| JP | 08271400 A | 10/1996 |
| JP | 2007040770 A | 2/2007 |

\* cited by examiner

ROTATIONAL RHEOMETER FOR MEASURING POWDERY OR GRANULAR MATERIALS

CROSS-REFERENCE TO RELATED APPLICATION

This application claims the priority, under 35 U.S.C. § 119, of Austrian patent application A 50196/2015, filed Mar. 11, 2015; the prior application is herewith incorporated by reference in its entirety.

BACKGROUND OF THE INVENTION

Field of the Invention

The invention relates to a rheometer for measuring powdery or granular materials, comprising a measuring container to hold the product to be measured and a cover for the measuring container and a measuring body driven by a measuring shaft, which is rotatable relative to measuring body in the container. The low friction measuring shaft, in particular contact-free, is led through the cover and arranged with a measuring system outside the measuring container to evaluate the measuring values received from the measuring shaft.

The invention has the object of creating a simply constructed rotational rheometer for measuring powders and/or bulk material and/or granular material and protecting both the user and sensitive components from any developing dust.

Rheometers for the rheological characterisation of powders are known. A measuring body is rotated or rotationally oscillated in a container containing the bulk or powder or particulate material to be examined, sometimes in combination with a linear movement of the measuring body, especially up or down, in the sample. The counteracting torque of the movement through the sample and/or the consequently appearing normal force are measured. Various embodiments of rheometers or viscometers are used which are equipped either as a universally applicable rheometer with special powder measurement cells, or it can be used directly with equipment specially produced for the application, often also with supplementary measurement possibilities, such as, for example, packing density and/or weight of the test substance, etc.

In this way, the powder can be measured both in a fluidized or dynamic state and in non-fluidized or static state. Arrangements are also known where the powder is prepressed under pressure or is also acted upon by pressure during the measurement. The sample preparation by fluidization enables the "removal of the powder memory", e.g. pouring effects, caking, etc., with associated static powder characterisation. In the dynamic mode, the powder is kept in a fluidized state during the measurement.

Japanese patent JP H 08271400 A discloses a system which measures the penetration depth of a conical rotor and the torque occurring for the characterisation of the powder and simultaneously carries out a fluidization of the powder in the measuring cup with means for vibrating the measuring cup.

Japanese published patent application JP 2007040770 discloses a system with the possibility of rotationally moving a measuring body through a powder in a measuring cup. An arrangement with compressed air which flows through the powder enables the fluidization of the powder.

Fluidization may also be brought about by vibration, for example by means of piezo elements, ultrasound or an unbalance motor. At the same time, this vibration may be used to adjust a specific powder level in the measuring cup. Fluidization and the "removal of the powder memory" ensures application-independent measurements.

What all devices have in common is that the measuring body is moved relative to the powder. This movement may be performed in rotation or in oscillating rotation. In this case, either the measuring cup may be rotated and the measuring body provided with means for determining the torque, or the measuring body may be rotated and the resultant torques determined, for example, by means of a measuring motor on the measurement shaft.

Optionally, the movement may be combined with a linear feed rate along the rotational axis, which then leads to a screw-like movement of the measuring body in the powder.

The measurement motor of a rheometer can then be used to record the normal forces and/or torques occurring at the measurement body. The evaluation is carried out analogously to the rheometer based on these measurement values, but phenomenological evaluations may also be carried out, e.g. an indication of the so-called flow energy (unit: Joule), as an integral of the torque over the rotation angle and/or the normal force over the displacement measured according to the method of the measuring body in the powder.

In order to carry out highly accurate measurements with a rheometer, the rotation of the measuring body must take place as smoothly as possible. Therefore, high demands are placed on the bearings of the measuring shaft which carries the measuring body; as a rule, the smoothest possible ball bearings, magnetic bearings, fluid bearings and the like, are used. The normal forces may be measured in various ways. The measuring cell may, for example, be designed as a "weighing cell" on the measuring cup, or measuring units may be arranged on the measuring motor or on the measuring body axis. Rheometers may, for example, also have special air bearings with integrated normal force measurement (see, commonly assigned U.S. Pat. No. 6,167,752 B1 and its counterpart Austrian patent document AT 404 192).

The measuring shaft should be as free of friction as possible from the driving motor to the measuring body, in particular supported without contact.

Also known are special rheometer embodiments that are designed to protect measuring shafts, bearings and drive motors against aggressive gases and/or moisture. This can be done, on the one hand, by seals that are as friction-free as possible. Stuffing boxes may be used, for example, to prevent the penetration of aggressive gases in the measurement motor; while labyrinth seals are also used for this.

In order to be able to perform powder measurements universally with such a rheometer, and in particular for fluidized powder, the use of a single such seal is not sufficient. The sensitive, mostly electronic measuring system must be protected especially by special measures against the ingress of dust. Further, the leakage of harmful powder from the measuring cell or the measuring range is to be avoided.

If the powder is in a fluidized state, then an aerosol forms above the powder bed, which consists of the fine fraction of the powder. In addition, upon fluidization, larger, heavier powder particles are projected towards the seal through implementation of the measurement shaft with high kinetic energy.

SUMMARY OF THE INVENTION

It is accordingly an object of the invention to provide a rheometer which overcomes the above-mentioned and other disadvantages of the heretofore-known devices and methods of this general type and to provide for the production of a powder rheometer that results in an accurate measured value with adequate dust protection. Without adequate dust protection, the application is usually limited to very special powder. Powder, which can only be poorly fluidized and forms large bursting powder bubbles on the passage of gases, is excluded as a rule from the investigation. The powder particles obtained by these bursting bubbles have very high kinetic energies and are projected in all directions and also out of the cup interior or measuring container against the measurement axis or shaft and/or bearing of the measuring motor or the components for torque measurement and/or the means for the normal force measurement.

If the powder particles are very fine, a labyrinth seal does not seal sufficiently. If the powder components have too much energy, a labyrinth seal can be filled by penetrating particles and fail.

Ball bearings, which are more resistant to the entry of powder dusts, may be damaged during the measurement of fine dust-forming powders. In addition, the torques generated with these arrangements cannot be determined sufficiently accurately.

The invention also has the main object of providing a dust cover for a rheometer so that universal powders of different composition, size distribution and fluidizability can be measured.

In addition, for reasons of operator safety, the powder may not be released in the device surroundings. Thus powder with aggressive components that pose a health risk for the operator may also be studied.

Another object of the invention is therefore to provide a powder measuring system or rheometer which prevents swirling and the release of powder components into the ambient air.

With the foregoing and other objects in view there is provided, in accordance with the invention, a rotational rheometer for measuring powdery or granular materials, the rheometer comprising:

- a measuring container for receiving a material to be measured and a cover for the measuring container;
- a measuring body held on a measuring shaft, wherein the measuring body and the container are rotatable relative to one another, and wherein the measuring shaft is guided through the cover with low friction or without contact;
- a sealing device disposed to seal a bearing gap or a passage of the measuring shaft in or through the cover, the sealing device including a fluid seal with a sealing fluid inlet and at least one geometric seal forming a powder barrier with the fluid seal; and
- an evaluation unit disposed outside the measuring container for evaluating measured values received by the measuring shaft.

In other words, according to the invention, a rheometer of the above-mentioned type is characterized in that both a fluid seal with a sealing-fluid supply line and at least one geometric seal interacting with this fluid seal as a powder barrier are provided to seal off the bearing gap or to implement the measuring shaft through the cover into the measuring container. According to the invention, a combination of at least two sealing principles or sealing variants is thus used to prevent leakage of powder from the measuring container and the ingress of powder components into the rheometer, and, in particular, into the evaluation electronics.

This prevents powder deposits occurring in the area of passages and bearings of the measuring shaft and thus creating additional frictional forces. This increases the repeatability of the measurement, and provides for the use of, for example, air bearings in the rheometer to offer the highest measurement accuracy with respect to the occurring torques.

The term "low friction" as used herein connotes an amount of frictional forces between the elements that may be neglected with regard to the measurement, or that may be integrated into the evaluation without negatively impacting the results of the evaluation. The term "without contact" means that no (or substantially no) mechanical, structural contact occurs between the parts while the rheometer is in operation.

It is inventively intended to provide a dust cover for a rheometer in the form of a combination of a fluid seal and a geometric barrier upon contact-free implementation of the measuring shaft through the cover of the measuring container. The sealing fluid used is preferably the same gas that is used for the fluidization of the powder. The geometric barrier keeps back the fine powder particles in the aerosol by means of fine channels or fine geometrical structures or interlocking teeth in the manner of a labyrinth seal for the sealing fluid. The problem of the use of only one type of seal is not sufficient to avoid complications arising during powder measurements is solved according to the invention. This solution was unexpected to persons skilled in the art, since a deterioration in the quality of the measurements was to be expected from the use of seals.

An easy-to-form geometric powder barrier can be provided, wherein the measuring shaft and the cover together preferably form a geometric powder barrier in the form of a fine sealing structure, preferably a labyrinth seal.

A fluid seal can be created without disturbing the measurement or negatively affecting the measurement results by the fluid seal containing a pressurised air supply line or the fluid seal comprising a device connected to the measuring container in order to generate a negative pressure so that in the bearing gap between the measuring shaft and the cover, in particular a gas flow of the sealing gas or ambient air is directed into the measuring container in the region under a fine powder geometric barrier.

An alternative fluid seal provides that a supply line to supply a gas pressure in the measuring container having a pressure exceeding that of the sealing gas is provided as a fluid seal in the region of the passage between the geometric powder barrier and the interior of the measuring container, in particular in the cover or the implementation of the measuring shaft.

One possibility for a fluid seal provides that at least one or more exhaust ports of a sealing-fluid supply line lies on the underside of the cover in the vicinity of the passage of the measuring shaft and/or is located above the shield, optionally wherein the sealing fluid flows through the outflow opening under pressure, or is sucked into the measuring container by the forming of 7 a negative pressure in the latter.

An advantageous geometric seal, in particular in combination with a labyrinth seal, is created when a shield is carried by the measuring shaft inside the measuring container as a geometric powder barrier, whose surface extension is at right angles to the measuring shaft and protrudes beyond all the sides of the opening.

Other features which are considered as characteristic for the invention are set forth in the appended claims.

Although the invention is illustrated and described herein as embodied in a rheometer, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
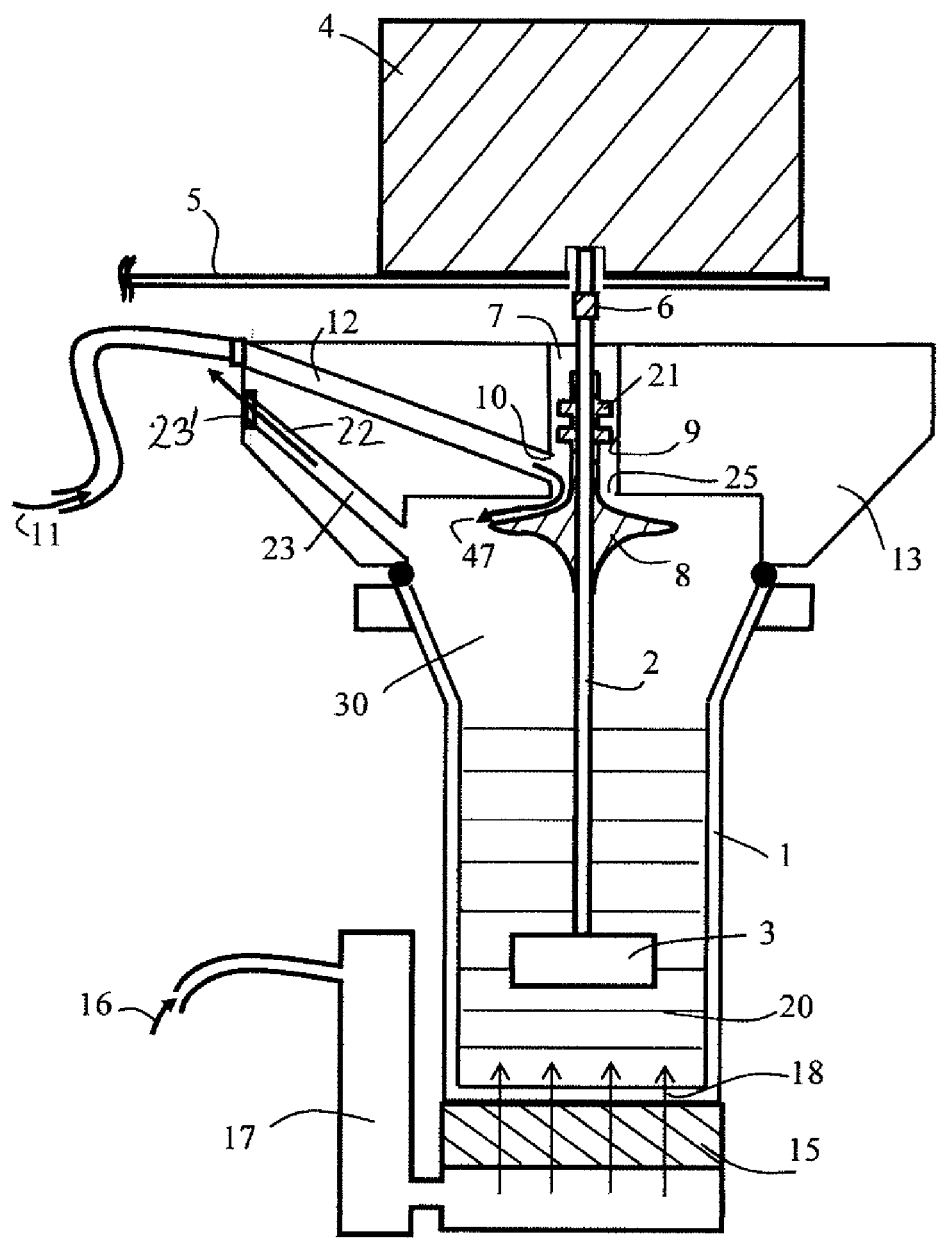
FIG. 1 shows a schematic section through an inventive rheometer having a measuring container with a fitted cover.

Referring now to the figures of the drawing in detail and first, particularly, to FIG. 1 thereof, there is shown a schematic view of an exemplary embodiment of a powder rheometer with a cylindrical measuring container 1, which simultaneously serves for the fluidization of the powder 20 to be examined. Compressed air is supplied along the arrow 16, for instance, via a line 17. The compressed air or other working gas is pumped into the measuring container 1 via the line 17 and a diffuser 15 according to the arrows 18. Various materials can be used 15 for the frit of the diffuser, which provides the respective turbulence matched to the powder to be measured 20.

A cover 13 is fitted, e.g. bolted or clamped, on the measurement cell or the measurement container 1. In addition to a combination of screws and a seal ring and screw, snap fasteners or flanged connections may be used. The measuring container 1 may also be formed of several parts, in order to allow it to be removed from the rheometer and the fluid system, and filled, weighed and/or cleaned.

A measuring shaft 2 is implemented by means of a passage 7 in the cover 13 of the measuring container 1, and carries a measuring body 3 in its lower end portion projecting into the measuring container 1. This measuring body 3 protrudes into the powder 20, and is connected via a coupling 6 to a drive or measurement motor 4, which is supported by a support 5 above the measuring container 1. The drive or measuring motor 4 rotates the measuring shaft 2 in the powder 20.

Arrangements related to the measurement of normal forces and/or torques occurring, or drives for the rotation of the drive or measuring motor 4 and any other raising and lowering of the measuring body 3, are not shown. An evaluation unit 40 for the readings is shown schematically in FIG. 2. All of these units, as well as the basic construction of rheometers, are known to the person skilled in the art.

The cover 13 is designed in the present case in one piece and has a bore or passage 7 in the center to receive and implement the measurement axis or shaft 2, which carries the measuring body 3. In this case, the measuring shaft 2 carries components of the geometric seal. The cover 13 has components of the geometric seal created, for example, through turning or milling, or carries parts of the geometric seal. In the present case, a labyrinth seal is shown between the measuring shaft 2 and the cover 13 with a gap 9, which may be utilised as an air guide. If necessary, this labyrinth seal can also be sectioned in the cover 13 through the formation of individual grooves. Advantageously, both the cover 13 and the measuring shaft 2 carry parts of the labyrinth profile. In particular, it is advantageous if the cover 13 is in several parts. In the case of a one-piece design of the cover 13, it is also important that the measuring shaft 2 can be implemented through the cover 13, and that a coupling system 6 is provided for the measuring motor 4 to receive the replaceable measuring body 3 and the measuring shaft 2. An air inlet 10 in the opening or passage 7 in the seal below the geometric seal is, for example, connected to the compressed air supply of the rheometer for the powder fluidization, wherein the entire geometrical seal can be flushed by air blown or aspirated through this. In this case, the air supply and the seal are preferably designed centrically symmetrical in order to affect the measurement as little as possible.

The measuring chamber 30, limited by the cylindrical measuring cup 1 and the cover 13, is vented through an exhaust channel 23. Symmetrical guidance of the air streams may also be effected here. The outflow end of the exhaust channel 23 can be closed by a replaceable and cleanable filter 45, which prevents the escape of fluidized powder fractions.

A mechanical splash guard or shield 8 acting as the geometric seal prevents the direct impingement of powder particles with high kinetic energy in the area around the passage 7 of the cover 13 or the entry of powder in the opening 25, and protects the labyrinth seal as well as the fluid seal.

Directly in an approximately parallel direction to the measurement axis or measuring shaft 2, accelerated powder particles with high kinetic energy can only be retained by the fluid seal or geometric seal through high fluid flow rates. However, such high flow rates would affect the powder fluid formed in the measuring container 1 and the measurement results. The shield 8 solves this problem.

The sealing system possessing multiple components comprises a seal with fine channels or thin fissures 21 while the shield 8 perfectly protects the measuring motor 4 and its bearings or the control unit 41 and the evaluation unit 40 as well as the normal force measurement unit, and, even in the event of failure of the fluid seal, powder dusts are trapped in the geometric fine structure equipped with fine channels.

Figure 4:
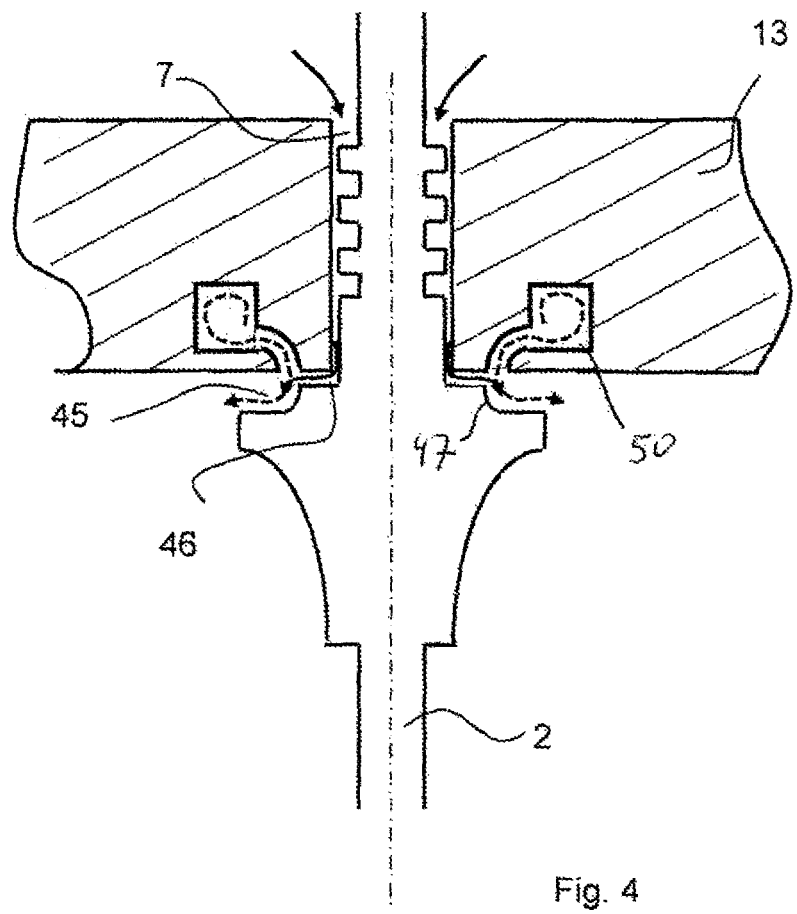
FIG. 4 shows an embodiment of a fluid seal.

By blowing the air in the passage 7, an air flow 47 is formed that is directed into the measuring container 1, and constitutes the air seal barrier. Preferably in the area near the outside of the shaft passage, a fine geometric structure provides that the sealing air preferably flows past in the direction of the measuring chamber or into the measuring container 1, and not outside the fine geometrical structure. According to the geometry, the movement of this air flow 45 possibly forms a Bernoulli vacuum in the seal structure and air is drawn inwards from the outside of the measuring chamber 30 by the seal structure. This airflow 45 flowing inside the seal structure ensures that no aerosol passes to the seal structure and the seal structure is thus not contaminated. The shield 8 can be designed geometrically so that the Bernoulli vacuum is maximised, as shown in FIG. 4.

By removing the measuring body 3 with the measuring shaft 2 and the shield 8, the elements located on the measuring shaft 2 of the seal structure can be cleaned.

Optionally, structures can also be applied to the measuring shaft 2 to form the geometric structure of the sealing bearing, for example, in the form of plastic parts that are created by rotating and/or milling or moulding. This allows the bearing components, which are moved by the measuring shaft 2, to be light in weight and, for example, pushed onto the measuring shaft 2. The structures may be adapted or applied even in the areas of the cover 13 lying within the region of the passage 7.

Alternatively, the measuring shaft 2 may be provided directly through turning and/or milling the geometrical structures for the seal.

Optionally, interchangeable measuring bodies 3 are used for various, e.g. aggressive or difficult-to-fluidize powders, or interchangeable powder sealing systems that are adapted to the measuring bodies 3.

It is also possible to measure the pressure drop across the sample and the powder 20 during the fluidization in the measuring container 1, e.g. by the pitot tube method.

Figure 2:
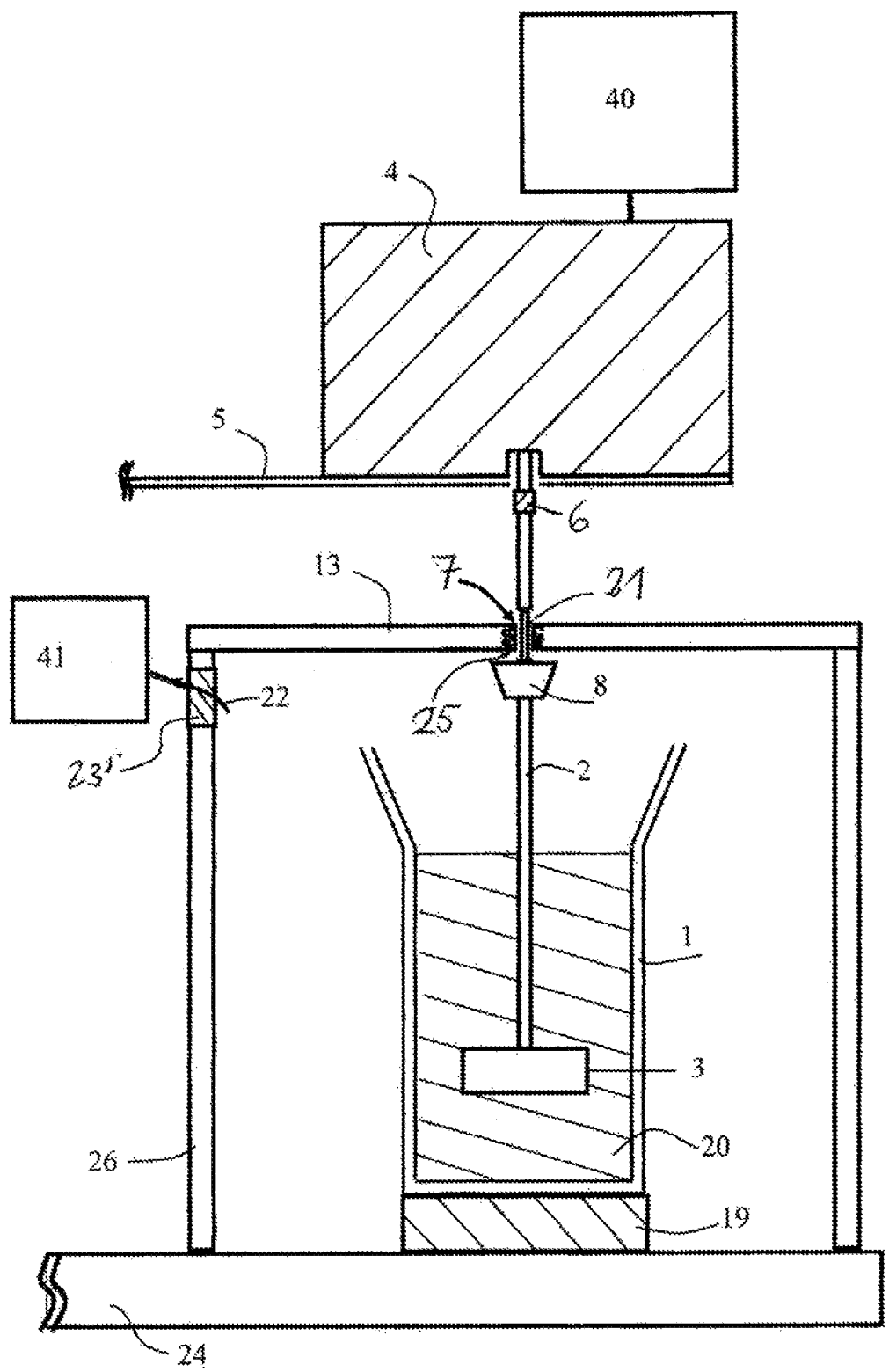
FIG. 2 shows a rheometer where the measuring container is surrounded by a sheath or an enveloping housing.

FIG. 2 shows a rheometer, whose measuring container 1 is surrounded by a tempering chamber 26. The tempering chamber 26 comprises a cover 13 as well as a jacket and a bottom part. In this case, the powder or dust is integrated into the cover 13 of the tempering chamber 26. The geometric seal is created here by interaction of the sealing geometry of the measuring shaft 2 and the cover 13 of the tempering chamber 26, or the formation and run of the gap 21.

The powder 20 in the measuring container 1 can be investigated in the tempering chamber 26 under specified environmental conditions, for example, humidity, temperature. A vibration generator 19 fluidizes the powder 20 in the measuring container 1. However, fluidization as shown in FIG. 1 is also conceivable here.

The shield 8 on the measuring shaft 2 has, for example, a trapezoidal cross-section here, and covers the opening 25 of the seal or passage 7. The sealing or passage 7 is designed in a similar way to the embodiment of FIG. 1.

Optionally, the tempering chamber 26 may have an outlet 23 for exhaust air with a filter assembly 23, through which the sealing fluid can enter the tempering chamber 26 through the passage 7 according to the arrow 22 by means of a suction unit 41.

Figure 3A:
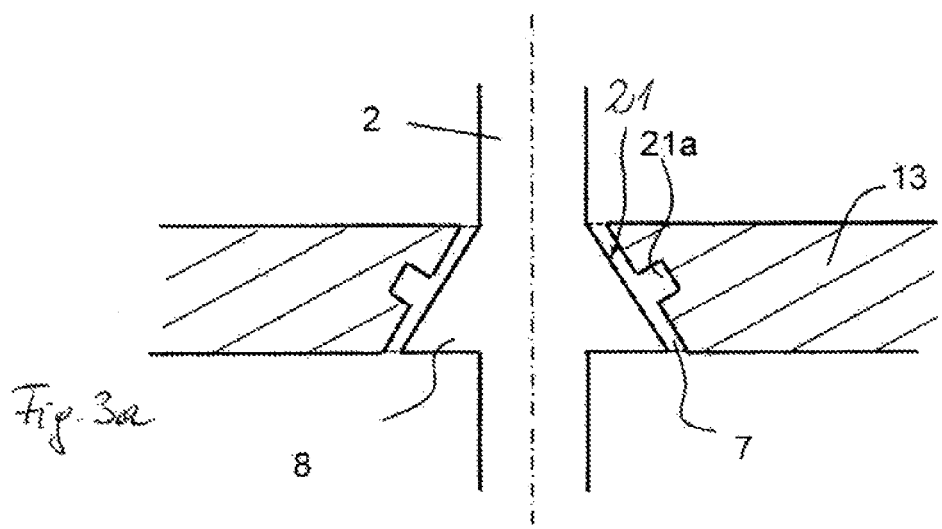
FIGS. 3A, 3B and 3C show variously shaped passages of the measuring shaft by a cover of the measuring container or an enveloping housing.

FIGS. 3a, b and c show different seal geometries for passage 7 with an airflow along the measuring shaft 2 in combination with a dust cover or a cover 13 of a measuring container 1 or a tempering chamber 26.

FIG. 3a shows a shield 8 located at the measurement axis, which, together with the cover 13, forms the gap 21 for the seal fluid. As an additional geometric fine structure, at least one fine geometric structure, such as a groove 21a is integrated in the cover 13.

Figure 3B:
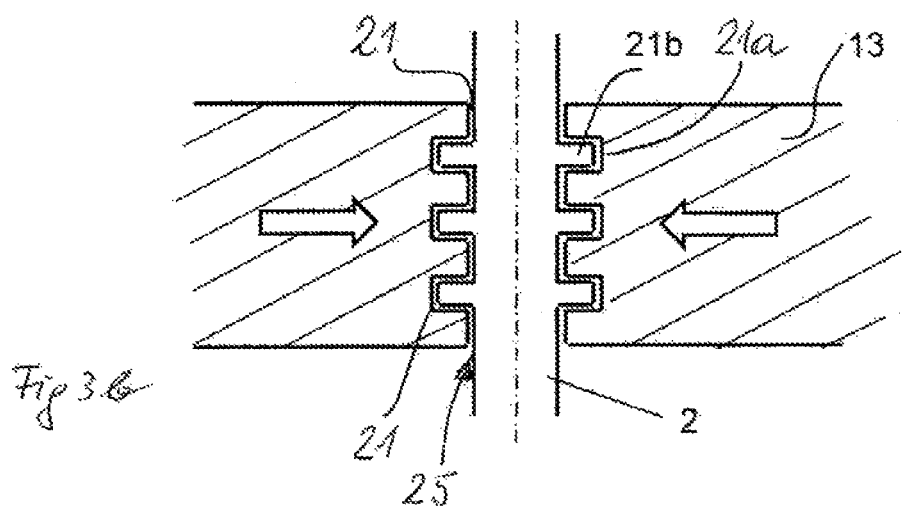

FIG. 3b shows an arrangement with a fine structure, which is supported by both the cover 13 and the measuring shaft 2. The geometric structures 21b together carried by the measuring shaft 2 form, together with the surrounding structure of the cover 13, a narrow gap 21. This may be used directly for the supply of air as described in FIG. 2, or the supply may be effected as in FIG. 1 with a channel (not shown here) for the fluid supply.

If the geometric fine structure, such as, for example, a labyrinth seal, is produced with an awkwardly angled gap 21 which is formed by the cover 13 and the sealing structure of the measuring shaft 2, the cover 13 must be made in two parts and positioned close to the measuring shaft in accordance with the arrows in order to enable the replacement of the measuring shaft 2 and thus the measuring body 3.

Figure 3C:
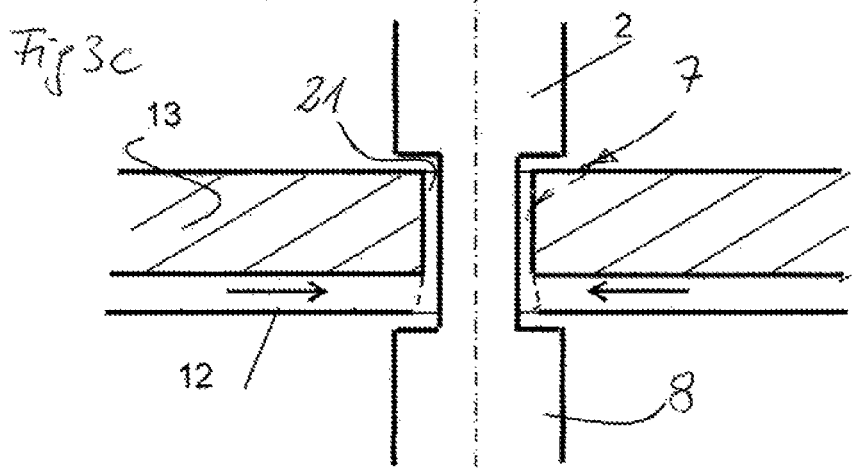

FIG. 3c shows an embodiment of the passage 7 which forms the shield 8 by tapering of the measuring shaft 2 at the passage 7. In any event, the fluid seal may be formed here by fluid lines 12 to the cover 13. Again, the cover 13 must be constructed in several parts in order to allow the removal of the measuring shaft 2. The shield 8 is formed by the measuring shaft 2.

FIG. 4 shows an arrangement wherein the shield 8 is so geometrically designed that the Bernoulli vacuum is maximised. In addition, the directed air flow 45 ensures through the geometrical seal that no aerosol reaches the seal structure and that the seal structure does not become contaminated. The guidance of the directed air flow 45 is maximised at approximately right angles to the opening 25 of the contact-free implementation of the measuring shaft 2 or the gap 46 formed between the underside of the cover 13 and the shield 8 in front of the gap 46 to provide the negative pressure and thus the Bernoulli effect that leads to a strongly directed flow of the air flowing through the passage 7 into the measuring chamber and the measuring container 1. The supply of the air flow 45 is via a channel 13 formed in the cover 50.

The rounded surface 47 at the upper end region of the shield 8 supports the air flow 45 and the formation of a vacuum.

The combination of a geometric seal with an air seal barrier is optimal to retain the fine fraction of the aerosol. The seal used here has a gap of only a few tenths of a millimeter between the cover of the container or its dust cover and the measuring system shaft and the measuring shaft 2. The air seal barrier comprises a gap or a supply port for a fluid on the inside of the cover or the dust protective cover of the enveloping housing, wherein the air stream flows inwards into the container, preferably uniformly, and steadily blows away the fine fraction from the gap or the supply port and the measuring shaft 2, but nevertheless only negligibly affects the measuring.

Preferably, the geometric seal or fine labyrinthine structure is effected on the motor side along and above the passage of the measuring shaft, i.e. also above a fluid supply for the fluid seal, wherein the fluid seal already recirculates the majority of the fine fraction of the powder into the interior of the measuring container.

In principle, the teeth of the geometric structure are not necessarily in the form of a labyrinth seal and do not form a "classical" labyrinth seal as in FIG. 3*b* when they engage with each other. The air flow resistance should be as high as possible when air or fluid flows outwards through the gap of the seal from the receiving chamber and from the interior of the measuring container 1. The combination of the fluid flow and the gap width must be so selected that the speed of the flushing gas has a sufficiently high kinetic energy to keep the aerosol and powder particles contained therein, outside the region of the shaft passage. A thin gap (a few millimeters, preferably a few tenths of a millimeter) and a flushing gas rate of a few m/s provides this high resistance, especially to powders of a particle size from a few nanometers up to particles in the order of magnitude of the gap width. The person skilled in the art may choose an optimal compromise between the gap width and the flushing gas rate as a function of the rheometer properties. Additional grooves and/or recesses in the cross-section of the seal and/or on the measuring shaft 2—see FIG. 3*a*, 3*b*, 3*c*—impede the aerosol which flows through the shaft passage and also prevents the formation of a laminar flow out of the measuring chamber. Preferably, the flushing gas is so selected in the passage, that the gas inlet is underneath the geometric seal or the grooves and the incoming air preferably flows towards the measuring chamber. The air particles or the aerosol can not flow simply or unimpeded from the measuring chamber through the gap, but are additionally blocked by eddies formed in the grooves. This is a geometric seal because the fluidized medium contains the fine fraction of the powder as suspended matter that cannot pass this type of passage, or only with difficulty.

Such geometrical barriers are particularly suitable for the retention of particles having a particle size much smaller than the passage gap width.

Preferably, a splash guard or shield can be used to cover the opening for the passage of the measuring shaft through the cover of the measuring container and that is supported by the measuring shaft 2 or the measuring container 1. This shield 8 also protects the gap of the seal or the passage from large heavy powder particles with high kinetic energy projected from the powder bed.

According to a combination of two geometric components, a shield 8 and a seal with a thin gap are optionally used in combination with an at least partially fluid-sealed enveloping housing around the measuring shaft and the measuring container.

The tempering of the powder sample may be effected, for example, by an air chamber whose implementation forms the proposed combination of fluid seal and geometric powder barrier, or via tempering elements directly on the measuring container 1 or on the cover 13 of the measuring container 1 or by supplying tempered humid gases for fluidization.

Essentially, the combination is of a fluid seal with additional geometric means or sealing structures. The fluid seal is formed substantially solely by the simple passage gap for the measuring shaft 2 with a through flow. In order to safely prevent the through flow of the powder or dust and particles with high kinetic energy, this fluid seal is combined with another geometric means. On the one hand, this may be the shield 8, which also has the function of limiting the inflow in the direction of the sample or measuring body 3, or, on the other, the fine structure with grooves to the geometry of a labyrinth seal.

For a powder rheometer, it is necessary for the fluid seal to be used in combination with other geometrical seal assemblies. A combination of all three variants described comprising the shield 8 of the high-energy, large particles and a fine structure for the smaller particles and dust particles and the fluid seal, is preferred. This ensures that no dust reaches the sensitive rheometer—indicated in the drawings with the measuring motor.

The fine structure may be arranged either above or below the fluid supply line, preferably above the fluid inlet as shown in FIG. 1 and FIG. 4.

The invention claimed is:

1. A rotational rheometer for measuring powdery or granular materials, the rheometer comprising:
 a measuring container for receiving a powdery or granular material to be measured and a cover for said measuring container;
 a measuring body held on a measuring shaft, wherein said measuring body and said container are rotatable relative to one another, and wherein said measuring shaft is guided through said cover without contact;
 a sealing device disposed to seal a bearing gap or a passage of said measuring shaft in or through said cover, said sealing device including a fluid seal with a sealing fluid supply line and at least one geometric seal forming a powder barrier with said fluid seal;
 said sealing device including a shield carried on said measuring shaft inside said measuring container and forming said geometrical powder barrier, said shield having a surface extension extending at right angles to said measuring shaft beyond an opening on all sides of said passage;
 at least one or more exhaust ports of said sealing fluid supply line formed on an underside of said cover in a vicinity of said passage of said measuring shaft and above said shield, or an air inlet issuing into said passage below a powder barrier disposed inside said cover; and
 an evaluation unit disposed outside said measuring container for evaluating measured values received by said measuring shaft.

2. The rotational rheometer according to claim 1, wherein the measuring shaft and the cover together form a fine seal structure as a further geometric powder barrier.

3. The rotational rheometer according to claim 2, wherein said fine seal structure is a labyrinth seal.

4. The rotational rheometer according to claim 1, wherein said fluid seal comprises a device connected to said measurement container and configured to generate a negative pressure, wherein outside air or sealing gas is aspirated into said measuring container through the gap of the passage between said measuring shaft and said cover.

5. The rotational rheometer according to claim 4, wherein the outside air or the sealing gas is aspirated into said measuring container through the gap in the region below the geometric powder barrier.

6. The rotational rheometer according to claim 1, wherein said fluid seal is formed in the region of the passage between said geometric powder barrier and an interior of said measuring container and said fluid seal comprises a supply line to supply a seal gas having a pressure exceeding a gas pressure in said measuring container.

7. The rotational rheometer according to claim 6, wherein said supply line terminates in said cover or said passage of said measuring shaft.

8. The rotational rheometer according to claim 1, wherein said shield is arranged at a spacing distance from said passage and wherein said spacing distance is smaller than a diameter of said passage or said shield is at least partially located in said passage.

9. The rotational rheometer according to claim 8, wherein said spacing distance is smaller than a radius of said passage.

10. The rotational rheometer according to claim 1, wherein said shield extends parallel to the opening of said passage.

11. The rotational rheometer according to claim 1, which comprises a unit disposed in said measuring container and configured for fluidizing the material to be measured.

12. The rotational rheometer according to claim 1, which comprises a unit connected to said measuring container and configured for fluidizing the material to be measured.

13. The rotational rheometer according to claim 1, wherein the sealing fluid flows through the outflow opening under pressure, or is aspirated into said measuring container by formation of a negative pressure in said measuring container.

14. The rotational rheometer according to claim 1, wherein the outflow opening is formed by a gap surrounding said measuring shaft.

15. The rotational rheometer according to claim 1, wherein said geometric seal is formed by grooves in said cover and/or in said measuring shaft.

* * * * *